(12) United States Patent
Rushbrooke et al.

(10) Patent No.: US 6,730,901 B1
(45) Date of Patent: May 4, 2004

(54) SAMPLE IMAGING

(75) Inventors: John Gordon Rushbrooke, Cambridge (GB); Claire Elizabeth Hooper, Cambridge (GB)

(73) Assignee: Packard Instruments Company Inc, Meriden, CT (US)

( * ) Notice: Subject to any disclaimer, the term of this patent is extended or adjusted under 35 U.S.C. 154(b) by 0 days.

(21) Appl. No.: 09/914,803

(22) PCT Filed: Jan. 25, 2000

(86) PCT No.: PCT/GB00/00212

§ 371 (c)(1),
(2), (4) Date: Apr. 27, 2002

(87) PCT Pub. No.: WO00/55601

PCT Pub. Date: Sep. 21, 2000

(30) Foreign Application Priority Data

Mar. 16, 1999 (GB) ................................. 9905954

(51) Int. Cl.⁷ .............................. H01J 3/14; G01J 1/04; G02B 6/04

(52) U.S. Cl. .................... 250/216; 250/227.11; 385/115

(58) Field of Search .............................. 250/216, 227.11, 250/461.1; 356/244, 436, 440, 442; 385/120, 116, 115

(56) References Cited

U.S. PATENT DOCUMENTS 6,542,241 B1 * 4/2003 Thorwirth et al. .......... 356/436
6,646,272 B2 * 11/2003 Rushbrooke et al. .... 250/461.1

FOREIGN PATENT DOCUMENTS

| GB | 2 315 130 | 1/1998 |
| WO | WO91/09300 | 6/1991 |
| WO | WO97/38329 | 10/1997 |
| WO | WO98/07022 | 2/1998 |

* cited by examiner

*Primary Examiner*—Stephone B. Allen
(74) *Attorney, Agent, or Firm*—Barnes & Thornburg

(57) ABSTRACT

An optical system for imaging a multiwell sample plate onto a CCD camera, wherein light from the illuminated sample plate (26) is imaged by one or more lenses (20,24) onto a fibre optic taper (22), bonded to the input face of the camera (28).

19 Claims, 3 Drawing Sheets

SAMPLE IMAGING

FIELD OF INVENTION

Figure 1:
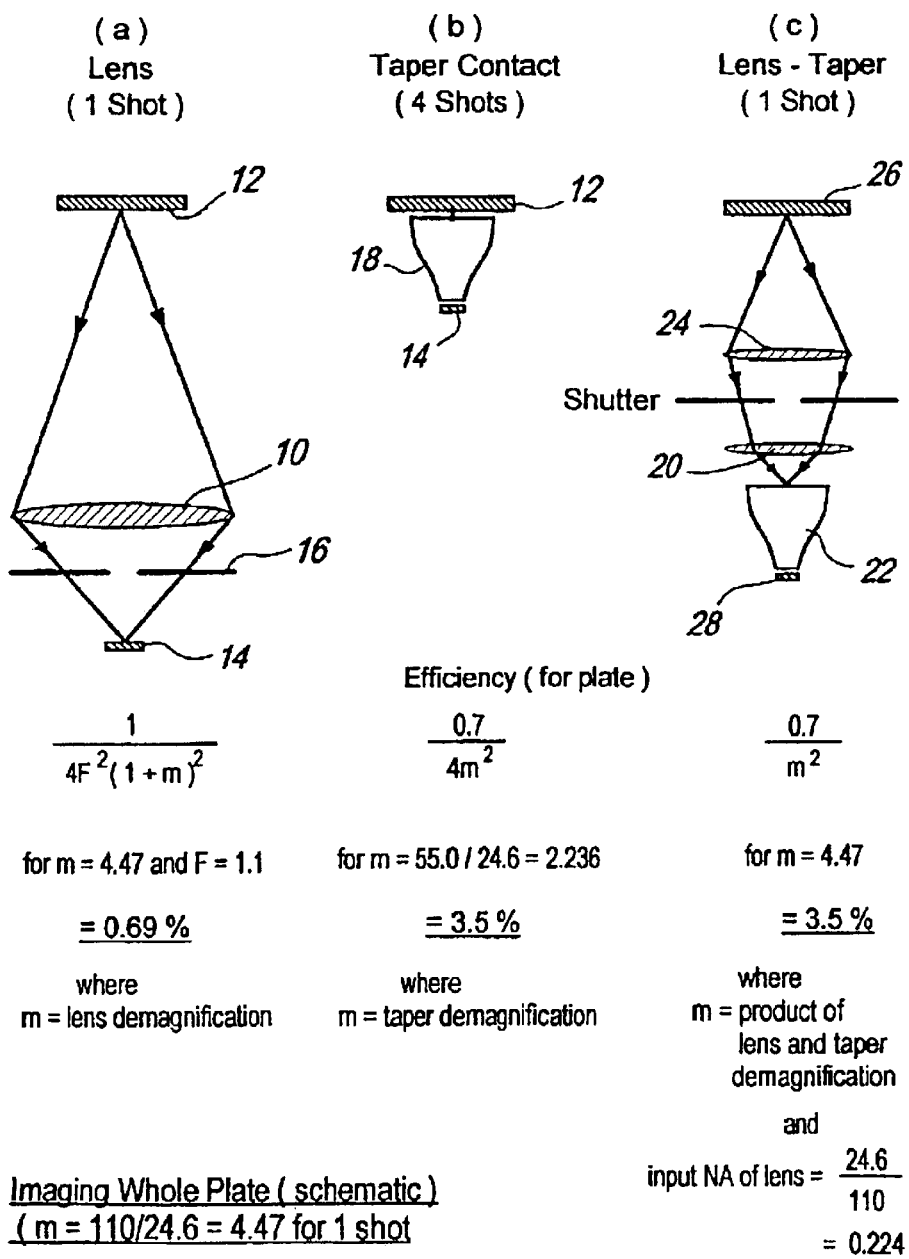

This invention concerns optical systems for imaging multiwell sample plates and the like onto camera devices, for analysis and monitoring of light activity in the wells.

BACKGROUND TO THE INVENTION

Biomedical samples, typically in multiwell sample plates, can be viewed and measured with a CCD camera using a suitable lens. The lens demagnification can be chosen to match the size of the whole sample plate (eg typically 110 mm ×75 mm), or a part of it, to the CCD. The CCD camera can be either a bare cooled CCD, or an image intensified CCD.

Typically a CCD camera sensor is 1" (25 mm) square. A demagnification of ~110/25=4.4 is therefore necessary to view a whole sample plate.

In modern biomedical assay chemistries where luminescent or fluorescent light emission occurs at long wavelengths towards the red end of the spectrum (600–700 mm) a bare cooled CCD has a great advantage. The CCD is cooled by Peltier or Cryogenic means to reduce the dark noise of the CCD sufficiently. Special electronics is needed to minimise read-out noise, but very low light levels can then be detected in the presence of low noise. The quantum efficiency of a CCD over most of the visible range is 35–40%. Using a thinned back-illuminated CCD, the efficiency can be as high as 8–90%.

The situation can be contrasted with image intensified CCD cameras, where photons are detected in the photocathode of the image intensifier. The quantum efficiency of typical low-noise photocathodes in the red is relatively poor (<5%). Where Gen1 image intensifiers are used, there is also usually shading, ie a fall-off of detection efficiency away from the centre of the field of view. Where Gen2 (microchannel plate) image intensifiers are used, there is also a problem at medium and high light levels, where the tube lifetime becomes limited. Gen3 image intensifiers offer much improved quantum efficiency in the red, but these are to some extent in the development stage, at least where tubes of reasonable diameter (eg 40 mm) are involved, and the noise level can be a problem.

With an image intensified CCD a single detected photon results in a burst of electrons in the CCD, spread over a number of pixels. Centroiding methods have been proposed to achieve sub-pixel spatial resolution (eg of the order of 10 microns) for locating the coordinates of a detected photon which is important in some imaging applications where many tiny light emitting sites are present in the sample, and the imaging process requires the different light emitting sites to be resolved the one from the other.

In general, centroiding methods cannot be used with a bare cooled CCD because a detected photon results in only a single electron in the silicon.

Instead of using a lens for imaging, a fibre optic taper can be employed to image the sample plate onto the CCD. A disadvantage however, is that multiple exposures are required to cover the entire plate.

THE INVENTION

According to one aspect of the present invention, a sample plate is imaged onto a CCD camera by the optical combination of at least one lens and a fibre-optic taper. A fibre optic taper possess some advantages and the use of a converging lens possesses other advantages. As will be apparent from later description however, the invention is able to achieve more than the sum of these differing advantages.

Preferably, the CCD camera is a bare cooled CCD.

Preferably a shutter or iris is included in the light path between the sample plate and the CCD camera.

Where a single lens is employed, the shutter may be located between the lens and the CCD camera faceplate. Where two lenses are employed the shutter may be located between the two lenses.

In general a multiwell sample plate can be imaged and analysed using a system embodying the invention, using a single exposure (shot), in contrast to the situation where a fibre optic taper is employed without a lens, when two or more exposures (shots) are generally required to form a complete image and analyse the entire sample plate.

A second lens may be incorporated to advantage, and typically an imaging lens is located close to the sample and a field lens is located close to the camera input faceplate.

More especially a system incorporating the invention is highly effective in light gathering. Efficiencies of the order of 3.5% can be envisaged.

Thus, preferably the field lens bends the light rays so as to be normal to the taper, hence minimising any loss of light due to rays entering the taper at angles outside the maximum acceptable angle $\theta=\sin^1$ (NA), where NA is the numerical aperture of the taper, (equal to the magnification), ie 24.6/70.7=0.348 in the example given above.

Moreover, in a preferred arrangement, efficient light gathering is achieved by bringing the sample plate as close as possible to the imaging lens and arranging the lens powers to cause the cone of light entering the fibre optic taper just to fill the numerical aperture (NA) of the taper.

In a first preferred embodiment, the taper is 110 mm diameter with a demagnification of 2.87. Lenses having an aperture of the order of F1.1 or better are preferred.

In general, the imaging lens will be a complex lens consisting of a number of separate lens components.

Preferably the light source is a laser light source.

In a further preferred arrangement a second field lens may be mounted close to the sample plate to select rays generally normal to the plate, even near to the edge of the plate, and thereby minimise parallax effects.

Either or both of the field lenses may be a simple single element lens or to advantage may be a multi-element lens.

In general, the imaging and field lenses will comprise a single, multi-component system possessing the property of telecentricity at object and image ie the ability to select rays that are on average normal to the object and image is parallax free.

DESCRIPTION OF EXAMPLES

Figure 2:
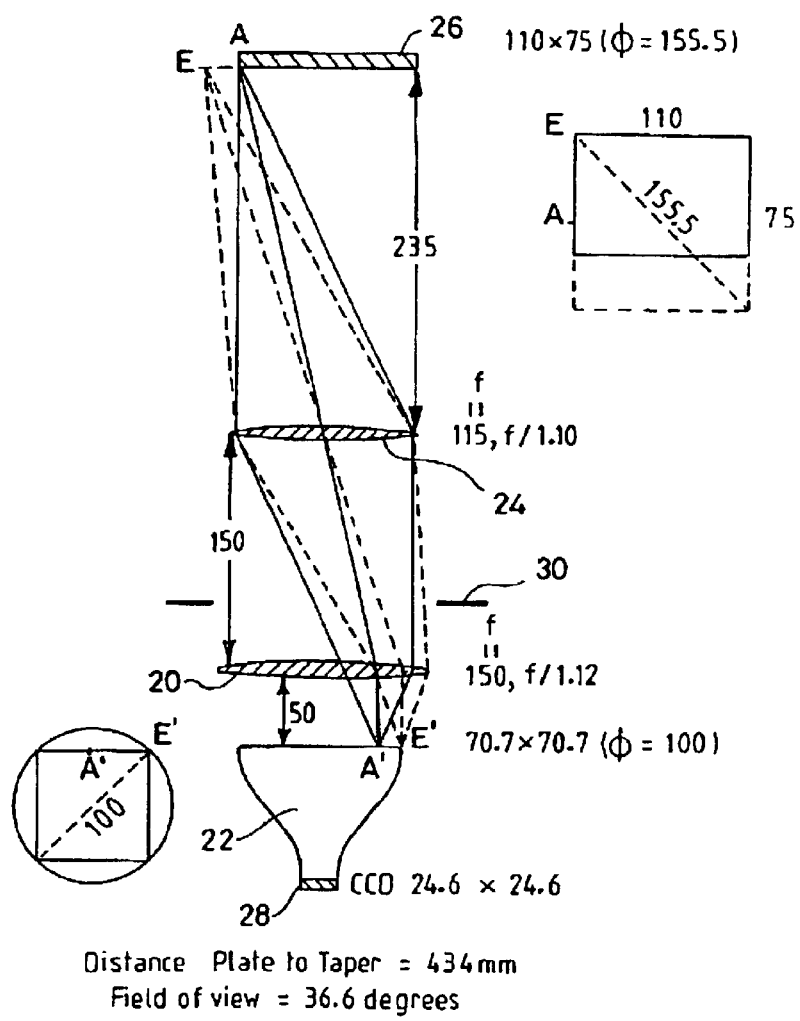
Figure 3:
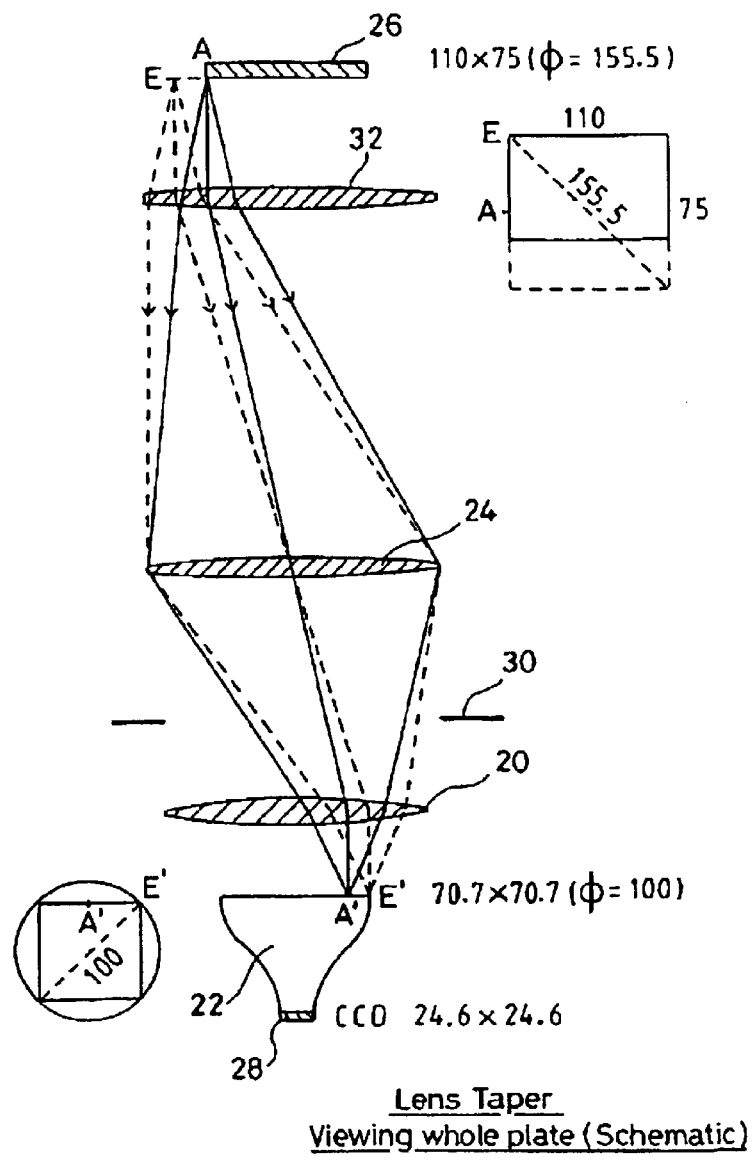

In the accompanying drawings:

FIGS. 1(a), (b) and (c) are provided to draw schematically a comparison between different possible arrangements; and FIGS. 2 and 3 show differing possible practical embodiments of a system embodying the invention.

It is assumed in FIGS. 1(a) and 1(c) that the lenses can be high quality multi-component lenses.

An example of one arrangement known in principle uses a bare cooled CCD and is shown schematically in FIG. 1(a).

It uses a lens 10 to image the sample plate 12 onto the CCD 14. A typical 1" CCD will have 1024×1024 pixels, the pixels being of size 24 microns×24 microns. A shutter 16 (or iris) is shown included in the light path to protect the CCD if a strong light source eg a laser, is being used to excite fluorescence in the sample, particularly if a time-resolved fluorescence method is being used (ie light on, light off, read sample, repeat).

In other circumstances, the shutter or iris may be employed to reduce frame shift smear such as when using self luminescent samples.

A generally known alternative to lens imaging is contact imaging, in which the sample plate 12 is presented directly to the CCD, via either a one-to-one thin fibre-optic plate to which the CCD may be bonded, or via a demagnifying taper to which the CCD may be bonded. This is shown in FIG. 1(*b*), in which a taper 18 (typically having an input diameter of 78 mm) enables a plate 12 to be viewed in four shots (or exposures). Contact imaging is to be preferred where higher light capture efficiency is desired. FIG. 1(*b*) shows a bare cooled CCD 14 but an image intensified CCD could instead be used.

The relative light gathering efficiency of lens imaging and taper contact imaging is also shown in FIGS. 1(*a*) and 1(*b*). In the case of a lens, the standard formula (in terms of the demagnification m and the ratio F of focal length:diameter) given in FIG. 1(*a*) applies. This means that in the example given an overall efficiency of only about 0.7% is obtained even with a very high quality F1.1 lens. The lens has the advantage that it can view the sample in one go. Also a shutter can be included as mentioned above. With taper contact imaging as depicted in FIG. 1(*b*), an efficiency of about 3% is obtainable, ie 4–5 times higher than for the lens. In the taper formula a factor 0.7 arises from the packing fraction of the fibres in the taper, a factor ¼ comes from the fact that 4 exposures are needed to view the whole plate, and there is a factor $1/m^2$, where m is the taper demagnification.

A preferred embodiment of lens-taper imaging embodying the invention is shown in FIG. 2 in which a field lens 20 bends the rays from the imaging lens 24 so as to be normal to the taper 22 so as to reduce parallax and light loss, ie the arrangement is telecentric. The imaging lens 24 focuses the sample plate 26 onto the CCD camera 28. The lens powers are selected so that the cone of light entering the taper 22 just occupies the numerical aperture of the taper. A shutter 30 is employed for the reasons given above. The optical path between the field lens 20 and the taper 22 is telecentric.

FIG. 1(*c*) contains a formula giving the efficiency of the arrangement shown in FIG. 2 for m=4.47, and demonstrates that the same efficiency of 3.5% that was obtained with the taper alone can be obtained with a lens-taper combination, provided the NA of the lens is chosen to fill the numerical aperture of the taper, which in this example means a less NA of 0.224.

The reason why a lens alone, as in FIG. 1(*a*), cannot be so efficient as the lens-taper arrangement of FIG. 1(*c*), is that the lens in FIG. 1(*a*) cannot fill the numerical aperture of the CCD which is unity, whereas the taper in FIG. 1(*b*) can have an output NA=1 and so match the CCD NA.

It is to be noted that another field lens of appropriate strength also could be inserted advantageously in front of the sample plate, that is between the sample plate and the imaging lens. This additional field lens receive light rays on average normal to the sample, and direct them to the imaging lens. This telecentric arrangement reduces parallax effects which can result in the loss of light being received from deep in the wells of a sample plate.

FIG. 3 shows a second field lens 32 mounted just beneath the sample plate 26 which collects rays that are on average normal to the plate. This collection of normal rays occurs across the whole area of the plate, even at the edges. As described above this telecentric arrangement minimises parallax effects, which can make it difficult otherwise to gather light from deep down a sample plate well. The imaging techniques illustrated here may be used to advantage in systems for analysing photon emitting assays such as described in UK Patent Specification No. 2294319.

It is to be noted that, in FIG. 2, the focal length and relative apertures are indicated, as well as the axial separator of the component. The corresponding details of the arrangement shown in FIG. 3 are readily calculatable, but will not be the same as the details marked in FIG. 2.

What is claimed is:

1. An optical system for imaging a sample plate onto a camera device, wherein the sample plate is imaged into a CCD camera by the optical combination of at least one lens through which light enters a fibre-optic taper, characterised in that the lens is a complex lens designed to be telecentric at least at its output, whereby light enters the taper at any point of its input face on average normal thereto.

2. A system according to claim 1, wherein the CCD camera is a bare cooled CCD camera or an intensified CCD camera.

3. A system according to claim 1, wherein the entire sample plate is imaged and analysed in a single exposure.

4. A system according to claim 1, wherein part of the sample plate is imaged at a time, so that the whole plate can be imaged and analysed by means of multiple exposures.

5. A system according to claim 1, wherein the taper gives a demagnification of the order of 2.87.

6. A system according to claim 1, wherein the complex lens is designed also to be telecentric at its input.

7. A system according to claim 1, using a laser light source to illuminate the sample.

8. A system according to claim 1, wherein the lens is a multi-component lens.

9. A system according to claim 8, wherein a shutter or iris is included in the light path between the sample and the CCD camera.

10. A system according to claim 9, wherein the shutter is located between the lens and the taper input, or between the sample and the lens.

11. A system according to claim 9, wherein the shutter is located between any pair of components of the multi-component lens.

12. A system according to claim 1, wherein the complex lens comprises an imaging lens located close to the sample and a field lens located close to the taper input.

13. A system according to clam 12, wherein the field lens acts to bend the light rays so as to be on average normal to the taper, hence minimising any loss of light due to rays entering the taper at angles outside the maximum acceptable angle $\theta=\sin^{-1}(NA)$, where NA is the numerical aperture of the taper, (equal to the magnification).

14. A system according to claim 12, wherein efficient light gathering is achieved by bringing the sample plate as close as possible to the imaging lens and arranging the lens powers to cause the cone of light entering the fibre optic taper at least substantially to fill the numerical aperture (NA) of the taper.

15. A system according to claim 12, wherein the light gathering efficiency is of the order of 3.5%.

16. A system according to claim 12, wherein the imaging lens has a numerical aperture sufficiently large to fill the numerical aperture of the taper.

17. A system according to claim 12, wherein the complex lens also includes a second field lens mounted close to the sample plate a select rays generally normal to the plate, even near to the edge of the plate, and thereby minimize parallax effects.

18. A system according to claim 17, wherein both field lenses are multi-element lenses.

19. A system for imaging a whole sample plate, or part thereof, comprising at least one complex lens through which light enters a fibre optic taper, wherein the lens is telecentric at least at its output and the power of the lens receiving light from the sample plate is arranged to cause the cone of light entering the taper to fall within the numerical aperture of a taper, the output face of which is bonded to a CCD camera.

* * * * *